(12) United States Patent
Dohrmann et al.

(10) Patent No.: US 11,213,224 B2
(45) Date of Patent: Jan. 4, 2022

(54) CONSUMER APPLICATION FOR MOBILE ASSESSMENT OF FUNCTIONAL CAPACITY AND FALLS RISK

(71) Applicant: Electronic Caregiver, Inc., Las Cruces, NM (US)

(72) Inventors: Anthony Dohrmann, El Paso, TX (US); Bryan John Chasko, Las Cruces, NM (US); David W. Keeley, Frisco, TX (US)

(73) Assignee: Electronic Caregiver, Inc., Las Cruces, NM (US)

( * ) Notice: Subject to any disclaimer, the term of this patent is extended or adjusted under 35 U.S.C. 154(b) by 135 days.

(21) Appl. No.: 16/289,551

(22) Filed: Feb. 28, 2019

(65) Prior Publication Data

US 2019/0282130 A1 Sep. 19, 2019

Related U.S. Application Data

(60) Provisional application No. 62/645,053, filed on Mar. 19, 2018.

(51) Int. Cl.
*A61B 5/11* (2006.01)
*A61B 5/00* (2006.01)

(52) U.S. Cl.
CPC .......... *A61B 5/1117* (2013.01); *A61B 5/0022* (2013.01); *A61B 5/1112* (2013.01); *A61B 5/742* (2013.01); *A61B 2562/0219* (2013.01)

(58) Field of Classification Search
CPC ..... A61B 5/1117; A61B 5/1114; A61B 5/112; A61B 5/1121; A61B 5/1122;
(Continued)

(56) References Cited

U.S. PATENT DOCUMENTS

| | | | |
|---|---|---|---|
| 5,211,642 | A | 5/1993 | Clendenning |
| 5,475,953 | A | 12/1995 | Greenfield |

(Continued)

FOREIGN PATENT DOCUMENTS

| | | | |
|---|---|---|---|
| CN | 104361321 A | 2/2015 | |
| CN | 106056035 A | 10/2016 | |

(Continued)

OTHER PUBLICATIONS

Machine translation of KR-20160040078-A, retrieved from Espacenet on Dec. 14, 2020. (Year: 2016).*

(Continued)

*Primary Examiner* — Patrick Fernandes
(74) *Attorney, Agent, or Firm* — Carr & Ferrell LLP

(57) ABSTRACT

Systems and methods for monitoring movement capabilities using clinical mobility based assessments of a user are provided herein. In embodiments, methods include: providing, using a mobile device comprising an inertial measurement device, a clinical mobility based assessment to a user; and generating, using the inertial measurement device, inertial data of the user that is indicative of movement capabilities of the user based on the clinical mobility based assessment. Embodiments include logging the inertial data of the user locally to the mobile device resulting in locally logged inertial data of the user; processing in real-time the locally logged inertial data of the user to determine position and orientation of the mobile device during the clinical mobility based assessment; and determining, using the position and the orientation of the mobile device during the clinical mobility based assessment, a physical movement assessment of the user associated with the clinical mobility based assessment.

16 Claims, 9 Drawing Sheets

(58) Field of Classification Search
CPC ............... A61B 5/1123; A61B 5/1124; A61B 2562/0219; A61B 5/742; A61B 5/0022; A61B 5/7275; G16H 10/60; G16H 50/20; G16H 50/30
See application file for complete search history.

(56) References Cited

U.S. PATENT DOCUMENTS

| | | |
|---|---|---|
| 6,665,647 B1 | 12/2003 | Haudenschild |
| 7,233,872 B2 | 6/2007 | Shibasaki et al. |
| 7,445,086 B1 | 11/2008 | Sizemore |
| 7,612,681 B2 | 11/2009 | Azzaro et al. |
| 7,971,141 B1 | 6/2011 | Quinn et al. |
| 8,206,325 B1 | 6/2012 | Najafi et al. |
| 8,771,206 B2 | 7/2014 | Gettelman et al. |
| 9,317,916 B1 | 4/2016 | Hanina et al. |
| 9,591,996 B2 | 3/2017 | Chang et al. |
| 9,972,187 B1 | 5/2018 | Srinivasan et al. |
| 10,387,963 B1 | 8/2019 | Leise et al. |
| 10,628,635 B1 | 4/2020 | Carpenter, II et al. |
| 10,813,572 B2 | 10/2020 | Dohrmann et al. |
| 11,113,943 B2 | 9/2021 | Wright et al. |
| 2002/0062342 A1 | 5/2002 | Sidles |
| 2002/0196944 A1 | 12/2002 | Davis et al. |
| 2004/0109470 A1 | 6/2004 | Derechin et al. |
| 2005/0035862 A1 | 2/2005 | Wildman et al. |
| 2005/0055942 A1 | 3/2005 | Maelzer et al. |
| 2007/0238936 A1 | 10/2007 | Becker |
| 2008/0010293 A1 | 1/2008 | Zpevak et al. |
| 2008/0186189 A1 | 8/2008 | Azzaro et al. |
| 2009/0094285 A1 | 4/2009 | Mackle et al. |
| 2010/0124737 A1 | 5/2010 | Panzer |
| 2011/0126207 A1 | 5/2011 | Wipfel et al. |
| 2011/0145018 A1 | 6/2011 | Fotsch et al. |
| 2011/0232708 A1 | 9/2011 | Kemp |
| 2012/0025989 A1 | 2/2012 | Cuddihy et al. |
| 2012/0075464 A1 | 3/2012 | Derenne et al. |
| 2012/0120184 A1 | 5/2012 | Fornell et al. |
| 2012/0121849 A1 | 5/2012 | Nojima |
| 2012/0154582 A1 | 6/2012 | Johnson et al. |
| 2012/0165618 A1 | 6/2012 | Algoo et al. |
| 2012/0179067 A1 | 7/2012 | Wekell |
| 2012/0179916 A1 | 7/2012 | Staker et al. |
| 2012/0229634 A1 | 9/2012 | Laett et al. |
| 2012/0253233 A1 | 10/2012 | Greene et al. |
| 2013/0000228 A1 | 1/2013 | Ovaert |
| 2013/0127620 A1 | 5/2013 | Siebers et al. |
| 2013/0145449 A1 | 6/2013 | Busser et al. |
| 2013/0167025 A1 | 6/2013 | Patri et al. |
| 2013/0204545 A1 | 8/2013 | Solinsky |
| 2013/0212501 A1 | 8/2013 | Anderson et al. |
| 2013/0237395 A1 | 9/2013 | Hjelt et al. |
| 2013/0289449 A1 | 10/2013 | Stone et al. |
| 2013/0303860 A1 | 11/2013 | Bender et al. |
| 2014/0128691 A1 | 5/2014 | Olivier |
| 2014/0148733 A1 | 5/2014 | Stone et al. |
| 2014/0171039 A1 | 6/2014 | Bjontegard |
| 2014/0171834 A1 | 6/2014 | DeGoede et al. |
| 2014/0232600 A1 | 8/2014 | Larose et al. |
| 2014/0243686 A1 | 8/2014 | Kimmel |
| 2014/0278605 A1 | 9/2014 | Borucki et al. |
| 2014/0330172 A1* | 11/2014 | Jovanov ............... A61B 5/6898 600/595 |
| 2014/0337048 A1 | 11/2014 | Brown et al. |
| 2014/0358828 A1 | 12/2014 | Phillipps et al. |
| 2014/0368601 A1 | 12/2014 | deCharms |
| 2015/0019250 A1 | 1/2015 | Goodman et al. |
| 2015/0109442 A1 | 4/2015 | Derenne et al. |
| 2015/0169835 A1 | 6/2015 | Hamdan et al. |
| 2015/0359467 A1 | 12/2015 | Tran |
| 2016/0026354 A1 | 1/2016 | McIntosh et al. |
| 2016/0154977 A1 | 6/2016 | Jagadish et al. |
| 2016/0217264 A1 | 7/2016 | Sanford |
| 2016/0253890 A1 | 9/2016 | Rabinowitz et al. |
| 2016/0267327 A1 | 9/2016 | Franz et al. |
| 2016/0314255 A1 | 10/2016 | Cook et al. |
| 2017/0000387 A1 | 1/2017 | Forth et al. |
| 2017/0000422 A1 | 1/2017 | Moturu et al. |
| 2017/0055917 A1 | 3/2017 | Stone et al. |
| 2017/0140631 A1 | 5/2017 | Pietrocola et al. |
| 2017/0147154 A1 | 5/2017 | Steiner et al. |
| 2017/0192950 A1 | 7/2017 | Gaither et al. |
| 2017/0193163 A1 | 7/2017 | Melle et al. |
| 2017/0197115 A1* | 7/2017 | Cook ............... A63B 24/0075 |
| 2017/0213145 A1 | 7/2017 | Pathak et al. |
| 2017/0337274 A1 | 11/2017 | Ly et al. |
| 2017/0344706 A1 | 11/2017 | Torres et al. |
| 2017/0344832 A1 | 11/2017 | Leung et al. |
| 2018/0075558 A1 | 3/2018 | Hill, Sr. et al. |
| 2018/0165938 A1 | 6/2018 | Honda et al. |
| 2018/0182472 A1 | 6/2018 | Preston et al. |
| 2018/0189756 A1 | 7/2018 | Purves et al. |
| 2018/0322405 A1 | 11/2018 | Fadell et al. |
| 2018/0360349 A9 | 12/2018 | Dohrmann et al. |
| 2018/0368780 A1 | 12/2018 | Bruno et al. |
| 2019/0029900 A1 | 1/2019 | Walton et al. |
| 2019/0042700 A1 | 2/2019 | Alotaibi |
| 2019/0057320 A1 | 2/2019 | Docherty et al. |
| 2019/0090786 A1 | 3/2019 | Kim et al. |
| 2019/0116212 A1 | 4/2019 | Spinella-Mamo |
| 2019/0130110 A1 | 5/2019 | Lee et al. |
| 2019/0164015 A1 | 5/2019 | Jones, Jr. et al. |
| 2019/0196888 A1 | 6/2019 | Anderson et al. |
| 2019/0220727 A1 | 7/2019 | Dohrmann et al. |
| 2019/0259475 A1 | 8/2019 | Dohrmann et al. |
| 2019/0286942 A1 | 9/2019 | Abhiram et al. |
| 2019/0311792 A1 | 10/2019 | Dohrmann et al. |
| 2019/0318165 A1 | 10/2019 | Shah et al. |
| 2019/0385749 A1 | 12/2019 | Dohrmann et al. |
| 2020/0101969 A1 | 4/2020 | Natroshvili et al. |
| 2020/0251220 A1 | 8/2020 | Chasko |
| 2020/0357256 A1 | 11/2020 | Wright et al. |
| 2021/0007631 A1 | 1/2021 | Dohrmann et al. |
| 2021/0273962 A1 | 9/2021 | Dohrmann et al. |

FOREIGN PATENT DOCUMENTS

| | | | |
|---|---|---|---|
| CN | 107411515 A | 12/2017 | |
| EP | 3815108 A1 | 5/2021 | |
| JP | 2002304362 A | 10/2002 | |
| JP | 2005228305 A | 8/2005 | |
| JP | 2016525383 A | 8/2016 | |
| KR | 20160040078 A * | 4/2016 | ............ H04M 19/04 |
| WO | WO-2014043757 A1 * | 3/2014 | ............ A61B 5/112 |
| WO | WO2018032089 A1 | 2/2018 | |
| WO | WO2019143397 A1 | 7/2019 | |
| WO | WO2019164585 A1 | 8/2019 | |
| WO | WO2019182792 A1 | 9/2019 | |
| WO | WO2019199549 A1 | 10/2019 | |
| WO | WO2019245713 A1 | 12/2019 | |
| WO | WO2020163180 A1 | 8/2020 | |
| WO | WO2020227303 A1 | 11/2020 | |

OTHER PUBLICATIONS

Bajaj, Prateek, "Reinforcement Learning", GeeksForGeeks.org [online], [retrieved on Mar. 4, 2020], Retrieved from the Internet:<URL:https://www.geeksforgeeks.org/what-is-reinforcement-learning/>, 7 pages.

Kung-Hsiang, Huang (Steeve), "Introduction to Various RL Algorithms. Part 1 (Q-Learning, Sarsa, DQN, DDPG)", Towards Data Science, [online], [retrieved on Mar. 4, 2020], Retrieved from the Internet:<URL:https://towardsdatascience.com/introduction-to-various-reinforcement-learning-algorithms-i-q-learning-sarsa-dqn-ddpg-72a5e0cb6287>, 5 pages.

Bellemare et al., A Distributional Perspective on Reinforcement Learning:, Proceedings of the 34th International Conference on Machine Learning, Sydney, Australia, Jul. 21, 2017, 19 pages.

Friston et al., "Reinforcement Learning or Active Inference?" Jul. 29, 2009, [online], [retrieved on Mar. 4, 2020], Retrieved from the Internet:<URL:https://doi.org/10.1371/journal.pone.0006421 PLoS One 4(7): e6421>, 13 pages.

(56) References Cited

OTHER PUBLICATIONS

Zhang et al., "DQ Scheduler: Deep Reinforcement Learning Based Controller Synchronization in Distributed SDN" ICC 2019—2019 IEEE International Conference on Communications (ICC), Shanghai, China, doi: 10.1109/ICC.2019.8761183, pp. 1-7.
"International Search Report" and "Written Opinion of the International Searching Authority," Patent Cooperation Treaty Application No. PCT/US2018/057814, dated Jan. 11, 2019, 9 pages.
"International Search Report" and "Written Opinion of the International Searching Authority," Patent Cooperation Treaty Application No. PCT/US2018/068210, dated Apr. 12, 2019, 9 pages.
"International Search Report" and "Written Opinion of the International Searching Authority," Patent Cooperation Treaty Application No. PCT/US2019/021678, dated May 24, 2019, 12 pages.
"International Search Report" and "Written Opinion of the International Searching Authority," Patent Cooperation Treaty Application No. PCT/US2019/025652, dated Jul. 18, 2019, 11 pages.
"International Search Report" and "Written Opinion of the International Searching Authority," Patent Cooperation Treaty Application No. PCT/US2019/034206, dated Aug. 1, 2019, 11 pages.
Rosen et al., "Slipping and Tripping: Fall Injuries in Adults Associated with Rugs and Carpets," Journal of Injury & Violence Research, 5(1), 61-69. (2013).
"International Search Report" and "Written Opinion of the International Searching Authority," Patent Cooperation Treaty Application No. PCT/US2020/031486, dated Aug. 3, 2020, 7 pages.
"International Search Report" and "Written Opinion of the International Searching Authority," Patent Cooperation Treaty Application No. PCT/US2020/016248, dated May 11, 2020, 7 pages.
"Office Action", Australia Patent Application No. 2019240484, dated Nov. 13, 2020, 4 pages.
"Office Action", Australia Patent Application No. 2018403182, dated Feb. 5, 2021, 5 pages.
"Office Action", Australia Patent Application No. 2018409860, dated Feb. 10, 2021, 4 pages.
Leber, Jessica, "The Avatar will See You Now", MIT Technology Review, Sep. 17, 2013, 4 pages.
"Office Action", India Patent Application No. 202027035634, dated Jun. 30, 2021, 10 pages.
"Office Action", India Patent Application No. 202027033121, dated Jul. 29, 2021, 7 pages.
"Office Action", Canada Patent Application No. 3088396, dated Aug. 6, 2021, 7 pages.
"Office Action", Japan Patent Application No. 2020-543924, dated Jul. 27, 2021, 3 pages [6 pages with translation].
"Office Action", Australia Patent Application No. 2019240484, dated Aug. 2, 2021, 3 pages.
"Office Action", China Patent Application No. 201880089608.2, dated Aug. 3, 2021, 8 pages [17 pages with translation].
"Office Action", Canada Patent Application No. 3089312, dated Aug. 19, 2021, 3 pages.
"Extended European Search Report", European Patent Application No. 18901139.8, dated Sep. 9, 2021, 6 pages.
"Office Action", Canada Patent Application No. 3091957, dated Sep. 14, 2021, 4 pages.
"Office Action", Japan Patent Application No. 2020-540382, dated Aug. 24, 2021, 7 pages [13 pages with translation].
"Extended European Search Report", European Patent Application No. 18907032.9, dated Oct. 15, 2021, 12 pages.
Marston et al., "The design of a purpose-built exergame for fall prediction and prevention for older people", European Review of Aging and Physical Activity 12:13, <URL:https://eurapa.biomedcentral.com/track/pdf/10.1186/s11556-015-0157-4.pdf>, Dec. 8, 2015, 12 pages.
Ejupi et al., "Kinect-Based Five-Times-Sit-to-Stand Test for Clinical and In-Home Assessment of Fall Risk in Older People", Gerontology (vol. 62), (May 28, 2015), <URL:https://www.karger.com/Article/PDF/381804>, May 28, 2015, 7 pages.
Festl et al., "iStoppFalls: A Tutorial Concept and prototype Contents", <URL:https://hcisiegen.de/wp-uploads/2014/05/isCtutorialdoku.pdf>, Mar. 30, 2013, 36 pages.
"Notice of Allowance", Australia Patent Application No. 2019240484, dated Oct. 27, 2021, 4 pages.

* cited by examiner

| Motion Task | Area of Assessment |
|---|---|
| Timed Up-and-Go | Static stability, dynamic stability, mobility and falls risk. |
| 30 second Chair Stand | Lower body muscular strength, Lower body muscular endurance and falls risk. |
| Four Stage Balance Test | Static stability, postural stability, and falls risk. |
| Gait Analysis | Dynamic stability, mobility and falls risk. |
| Functional Reach Test | Balance, stability, limits of stability and falls risk |
| Sit and Reach Test | Lower body flexibility. |
| 5 Chair Stand Test | Lower body muscular strength. |
| 10 Chair Stand Test | Lower body muscular strength and muscular endurance. |
| Arm Curl Test | Upper extremity muscular strength and upper extremity muscular endurance. |
| Postural Stability | Static stability |

FIG. 5A

| Motion Task | Extracted Features |
|---|---|
| Timed Up-and-Go | Time to completion, rate to complete standing task, rate to complete sitting task, turn rate, anteroposterior sway, mediolateral sway, gait characteristics (see gait). |
| 30 second Chair Stand | Total repetitions, time rate of repetition completion decay, anteroposterior sway, mediolateral sway. |
| Four Stage Balance Test | Anteroposterior sway, mediolateral sway, total magnitude of displacement, success/failure of stage completion. |
| Gait | Cadence, linear velocity, stride length, step length, stance and swing times. |
| Functional Reach Test | Resultant displacement, vertical displacement, mediolateral displacement. |
| Sit and Reach Test | Resultant displacement, vertical displacement, mediolateral displacement. |
| 5 Chair Stand Test | Total repetitions, time rate of repetition completion decay, anteroposterior sway, mediolateral sway. |
| 10 Chair Stand Test | Total repetitions, time rate of repetition completion decay, anteroposterior sway, mediolateral sway. |
| Arm Curl Test | Total repetitions, time rate of repetition completion decay, resultant displacement, mediolateral displacement. |
| Postural Stability | Anteroposterior sway, mediolateral sway, total magnitude of displacement. |

FIG. 5B

CONSUMER APPLICATION FOR MOBILE ASSESSMENT OF FUNCTIONAL CAPACITY AND FALLS RISK

RELATED APPLICATION

This application claims the priority benefit of U.S. Provisional Application Ser. No. 62/645,053, filed on Mar. 19, 2018 titled "Consumer Application for Mobile Assessment of Functional Capacity and Falls Risk," which is hereby incorporated by reference herein in its entirety including all appendices and all references cited therein.

FIELD OF INVENTION

The present technology relates to a connected device software application. More specifically, but not by limitation, the present technology relates, to an application capable of assessing a user's real-time fall risk when installed onto a commercially available mobile device equipped with inertial measurement capabilities, having Internet and/or cellular connectivity, and voice communication technology.

BACKGROUND

The approaches described in this section could be pursued, but are not necessarily approaches that have previously been conceived or pursued. Therefore, unless otherwise indicated, it should not be assumed that any of the approaches described in this section qualify as prior art merely by virtue of their inclusion in this section.

In response to the numerous risks associated with aging, and the fact that the population of the United States is rapidly aging, the effort to maintain independence has led to the development of a number of applications focused on various aspects of health monitoring. Most of these applications have been developed in a manner such that they include capabilities for monitoring biological factors such as; blood pressure, heart rate, blood glucose levels, and/or sleep. While evidence suggests these biological signals associated with overall health and that consistent monitoring of parameters such as these can contribute to improved health, currently available health applications do not provide the capability to consistently monitor a user's capacity for producing motion. Additionally, these current health monitoring applications are generally not self-contained and many times require hardware in additional to that on which they have been installed. The present technology provides a self-contained comprehensive method of evaluating a user's movement capabilities and provides non-invasive methods to directly monitor and identify declines in functional capacity. The results of these critical motion assessments can be easily accessed by the user and displayed on the user's mobile device in various formats.

SUMMARY

In some embodiments the present disclosure is directed to a system of one or more computers which can be configured to perform particular operations or actions by virtue of having software, firmware, hardware, or a combination thereof installed on the system that in operation causes or cause the system to perform actions and/or method steps as described herein.

According to some embodiments the present technology is directed to a method for monitoring movement capabilities of a user using clinical mobility based assessments, the method comprising: (a) providing, using a mobile device comprising an inertial measurement device, a clinical mobility based assessment to a user; (b) generating, using the inertial measurement device, inertial data of the user that is indicative of movement capabilities of the user based on the clinical mobility based assessment; (c) logging the inertial data of the user locally to the mobile device resulting in locally logged inertial data of the user; (d) processing in real-time the locally logged inertial data of the user to determine position and orientation of the mobile device during the clinical mobility based assessment; (e) determining, using the position and the orientation of the mobile device during the clinical mobility based assessment, a physical movement assessment of the user associated with the clinical mobility based assessment; and (f) displaying, using the mobile device, at least a portion of the physical movement assessment to the user.

In various embodiments the method includes displaying a representation of the clinical mobility based assessment via an interactive animated conversational graphical user interface displayed by the mobile device.

In some embodiments the method includes the clinical mobility based assessment includes one or more of a test duration, a turning duration, a sit-to-stand duration, a stand-to-sit duration, a number of sit-to-stand repetitions completed within a predetermined period of time, and a number of stand-to-sit repetitions completed within a predetermined period of time.

In various embodiments the inertial data of the user that is indicative of movement capabilities of the user based on the clinical mobility based assessment comprises gyroscope data generated using a gyroscope; and accelerometer data generated using an accelerometer.

In some embodiments the processing in real-time the locally logged inertial data of the user to determine position and orientation of the mobile device during the clinical mobility based assessment comprises: segmenting and aligning the locally logged inertial data of the user resulting in segmented and aligned inertial data of the user; gravitational acceleration counterbalancing of the segmented and aligned inertial data of the user resulting in counterbalanced inertial data of the user; determining velocity of the mobile device during the clinical mobility based assessment using the counterbalanced inertial data of the user; drift compensating the velocity of the mobile device during the clinical mobility based assessment resulting in drift compensated velocity data; and determining the position and the orientation of the mobile device during the clinical mobility based assessment using the drift compensated velocity data.

In various embodiments the processing in real-time the locally logged inertial data of the user to determine position and orientation of the mobile device during the clinical mobility based assessment comprises: segmenting and aligning the locally logged inertial data of the user resulting in segmented and aligned inertial data of the user; integrating angular orientation of the segmented and aligned inertial data of the user resulting in counterbalanced inertial data of the user; determining velocity of the mobile device during the clinical mobility based assessment using the counterbalanced inertial data of the user; drift compensating the velocity of the mobile device during the clinical mobility based assessment resulting in drift compensated velocity data; and determining the position and the orientation of the mobile device during the clinical mobility based assessment using the drift compensated velocity data.

In some embodiments the method further comprises: determining features of functional movements of the user based on the position and the orientation of the mobile device during the clinical mobility based assessment, the features of functional movements including one or more of: time to completion of a task, rate to completion of a task, total repetitions of a task completed within a predetermined period of time, decay of repetitions of a task completed within a predetermined period of time, turn rate, anteroposterior sway, mediolateral sway, gait characteristics, total magnitude of displacement, vertical displacement, mediolateral displacement, and resultant displacement.

In various embodiments the physical movement assessment to the user includes one or more of a static stability of the user, dynamic stability of the user, postural stability of the user, balance of the user, mobility of the user, fall risk of the user, lower body muscular strength of the user, lower body muscular endurance of the user, lower body muscular flexibility of the user, upper body muscular strength of the user, and upper body muscular endurance of the user.

In some embodiments the method further comprises: receiving the locally logged inertial data of the user and the physical movement assessment of the user; conducting a longitude physical movement assessment analysis using the physical movement assessment of the user associated with the clinical mobility based assessment; and displaying at least a portion of the longitude physical movement assessment analysis to the user.

DESCRIPTION OF THE DRAWINGS

Certain embodiments of the present technology are illustrated by the accompanying figures. It will be understood that the figures are not necessarily to scale. It will be understood that the technology is not necessarily limited to the particular embodiments illustrated herein.

FIG. 5A depicts a table showing movement assessments for determining functional movement capacity of a user according to embodiments of the present technology.

FIG. 5B depicts a table showing features extracted from inertial data of the user that describe functional movements following application analysis algorithms describing user functional movement capacity according to embodiments of the present technology.

DETAILED DESCRIPTION

The detailed embodiments of the present technology are disclosed here. It should be understood, that the disclosed embodiments are merely exemplary of the invention, which may be embodied in multiple forms. Those details disclosed herein are not to be interpreted in any form as limiting, but as the basis for the claims.

In various embodiments an object of the present technology is a software application to provide monitoring and assessment of functional motion capacity of a user through simple interaction with an inertial measurement unit equipped mobile device. As such, the software application functions to consistently evaluate the motion characteristics of a user and report how those motion characteristics relate to the real-time functional capacity of the user. The software application also provides a user with the capability for assessing performance on a variety of fundamental movement tests. Additionally, the capacity of the software application to utilize cloud-based storage and compute functionality provides the capability for quick storage, retrieval and assessment of multiple tests in such a manner that real-time declines in functional movement capacity can be identified and reported. Additional advantages of the software application are apparent from the detailed embodiment descriptions and accompanying drawings, which set forth embodiments of the present technology.

Figure 1:
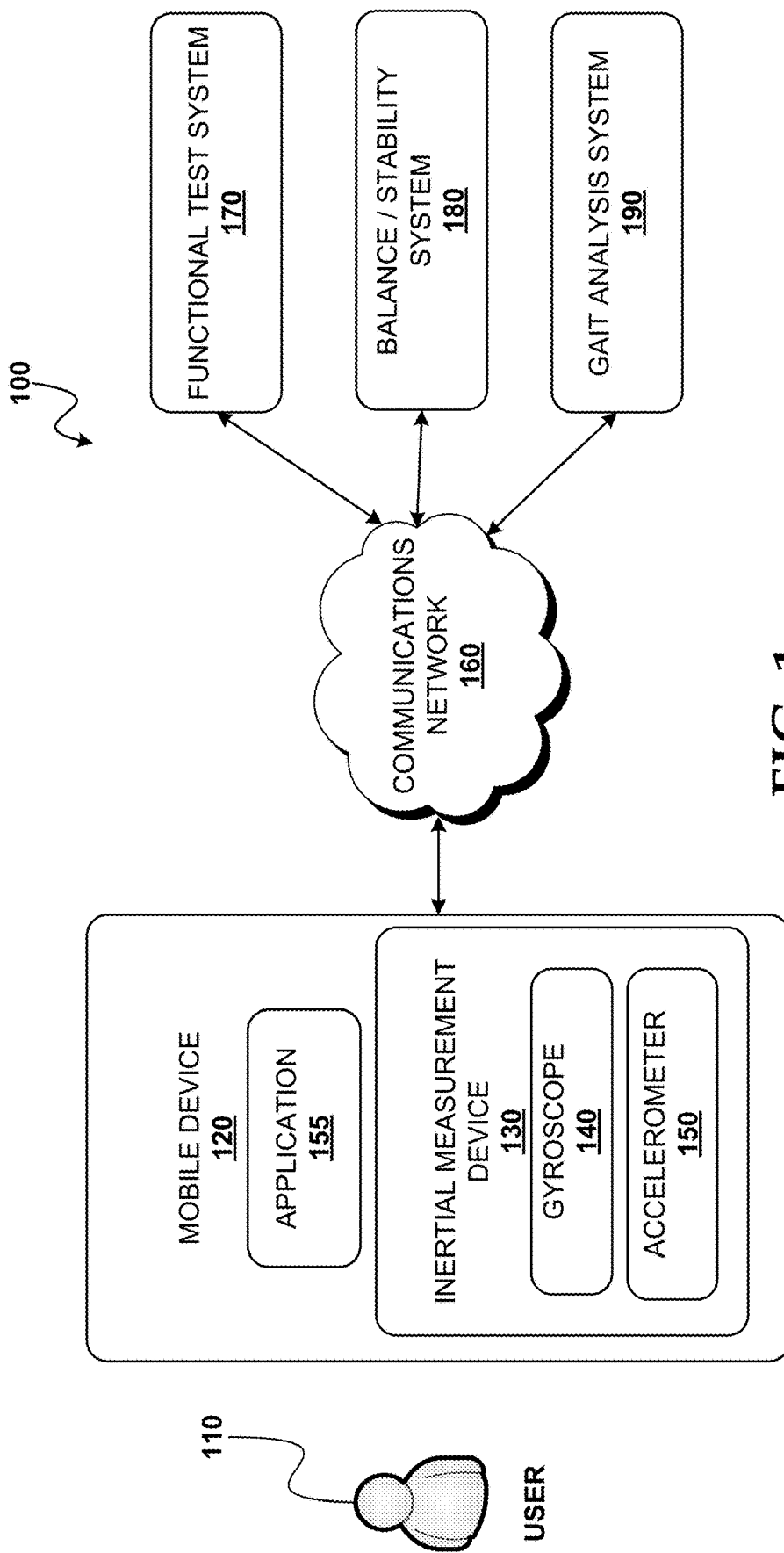
FIG. 1 shows a system for monitoring movement capabilities of a user using clinical mobility based assessments according to embodiments of the present technology.

FIG. 1 shows system 100 for monitoring movement capabilities of a user using clinical mobility based assessments according to embodiments of the present technology. The system 100 shows a user 110 that may access a mobile device 120. The mobile device 120 comprises an inertial measurement device 130. The inertial measurement device 130 may be a chip, and the like, installed on the mobile device 120. The inertial measurement device 130 comprises a gyroscope 140 and an accelerometer 150. The mobile device 120 further comprises an application 155 (e.g., a software application). The mobile device 120 uses a communications network 160 for communication with one or more of functional test system 170, balance/stability system 180, and gait analysis system 190.

In various embodiments the application 155 is an Electronic Caregiver developed mobile application capable of monitoring the movement capabilities of the user 110. When in use, the application 155 embodies the capability for the collection, processing, storage, and analysis of data describing motion characteristics of the user 110 during various clinical mobility based assessments. For example, a clinical mobility based assessment may be a motion task. In various embodiments a clinical mobility based assessment may be a test duration, a turning duration, a sit-to-stand duration, a stand-to-sit duration, a number of sit-to-stand repetitions completed within a predetermined period of time, and a number of stand-to-sit repetitions completed within a predetermined period of time. For example, the clinical mobility based assessments described in FIG. 5A and FIG. 5B. Exemplary clinical mobility based assessments (e.g., motion tasks) include timed up-and-go test, 30 second chair stand test, four stage balance test, gait analysis, functional reach test, sit and teach test, 5 chair stand test, 10 chair stand test, arm curl test, and postural stability using the mobile device 120 communicating with the functional test system 170, the balance/stability system 180, and the gait analysis system 190.

In various embodiments the user 110 may access the mobile device 120 by accessing a display of a representation of the clinical mobility based assessment via an interactive animated conversational graphical user interface displayed by the mobile device 120. Embodiments of the present technology include providing, using the mobile device 120 comprising the inertial measurement device 130, a clinical mobility based assessment to a user and generating, using the inertial measurement device 130, inertial data of the user 110 that is indicative of movement capabilities of the user 110 based on the clinical mobility based assessment. Embodiments comprise logging the inertial data of the user 110 locally to the mobile device 120 resulting in locally logged inertial data of the user 110. In various embodiments the inertial data of the user 110 that is indicative of movement capabilities of the user 110 based on the clinical mobility based assessment comprises gyroscope data generated using the gyroscope 140; and accelerometer data generated using the accelerometer 150.

Figure 2:
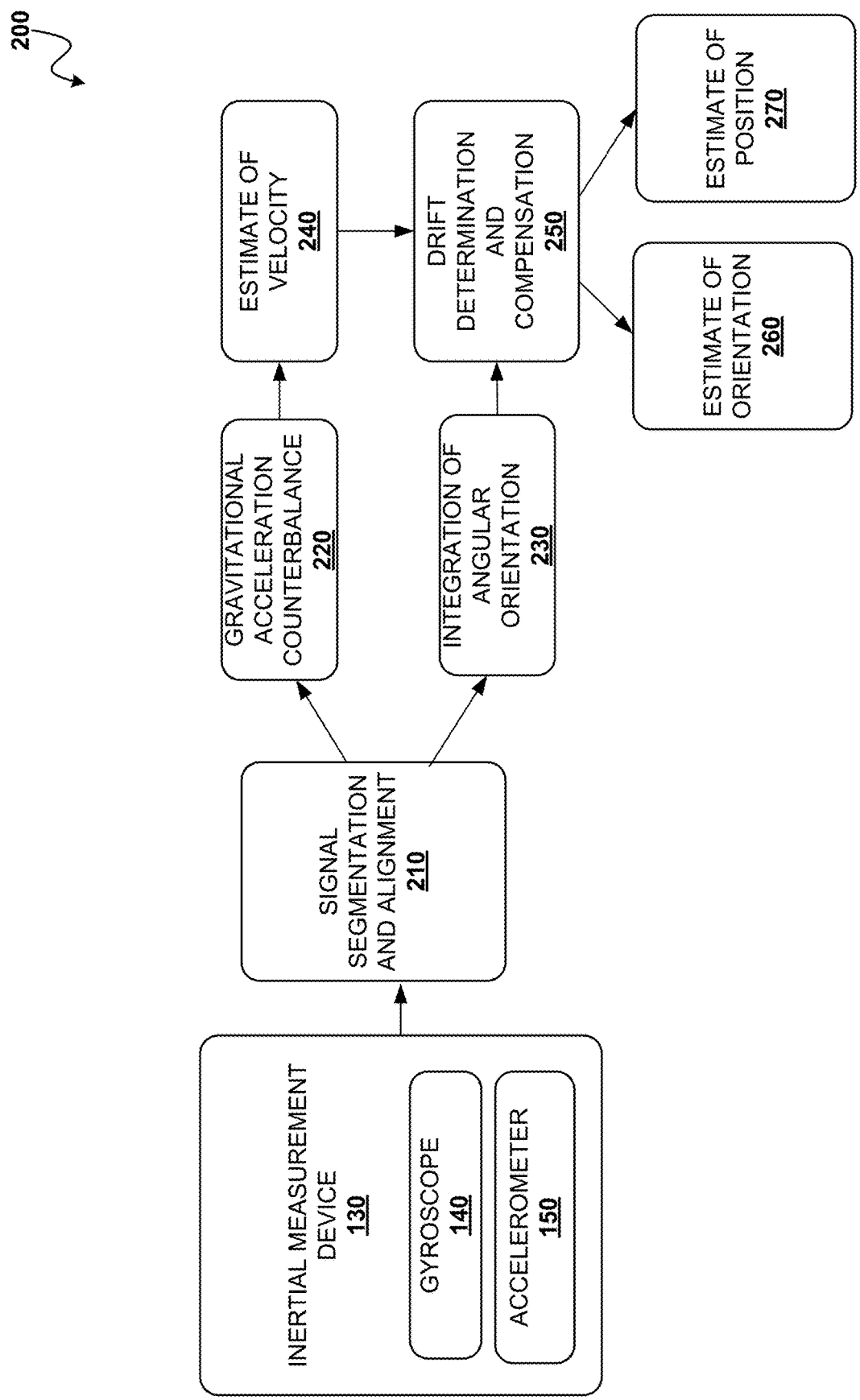
FIG. 2 illustrates an exemplary inertial data processing algorithm according to embodiments of the present technology.

FIG. 2 illustrates an exemplary inertial data processing algorithm 200 according to embodiments of the present technology. The inertial data processing algorithm 200 may be performed by processing logic that may comprise hardware (e.g., dedicated logic, programmable logic, and microcode), software (such as software run on a general-purpose computer system or a dedicated machine), or a combination thereof. In one or more example embodiments, the processing logic resides at the mobile device 120, the inertial measurement device 130, the functional test system 170, the balance/stability system 180, and the gait analysis system 190, or the cloud-based normative data storage 330 or combinations thereof. The inertial data processing algorithm 200 receives inertial data from the mobile device 120 comprising the inertial measurement device 130. The inertial measurement device 130 comprises the gyroscope 140 and the accelerometer 150. The inertial data processing algorithm 200 comprises signal segmentation and alignment 210, gravitational acceleration counterbalance 220, integration of angular orientation 230, estimate of velocity 240, drift determination and compensation 250, estimate of orientation 260, and estimate of position 270.

Figure 4A:
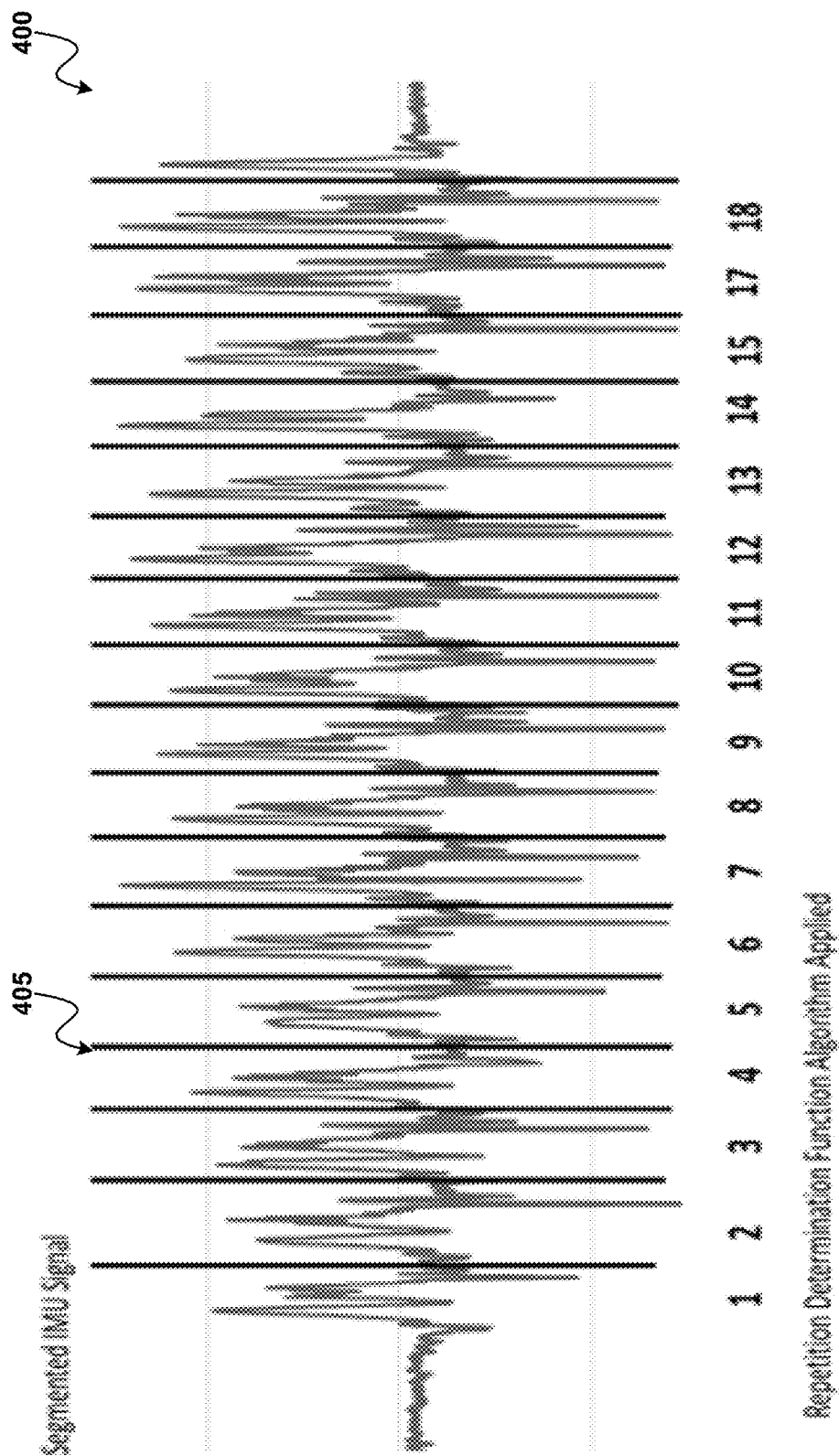
FIG. 4A shows results of an inertial data processing algorithm for analysis of a chair stand clinical mobility based assessment according to embodiments of the present technology.

In various embodiments the inertial data processing algorithm 200 is for monitoring movement capabilities of the user 110 using clinical mobility based assessments. Embodiments of the present technology include processing in real-time the locally logged inertial data of the user 110 to determine position and orientation of the mobile device 120 during the clinical mobility based assessment. In some embodiments the processing in real-time the locally logged inertial data of the user 110 to determine position and orientation of the mobile device during the clinical mobility based assessment comprises: segmenting and aligning the locally logged inertial data of the user 110 resulting in segmented and aligned inertial data of the user 110. For example, segmenting and aligning the locally logged inertial data of the user 110 is shown in FIG. 4A. Embodiments further include gravitational acceleration counterbalancing of the segmented and aligned inertial data of the user 110 resulting in counterbalanced inertial data of the user 110; determining velocity of the mobile device during the clinical mobility based assessment using the counterbalanced inertial data of the user 110; drift compensating the velocity of the mobile device during the clinical mobility based assessment resulting in drift compensated velocity data; and determining the position and the orientation of the mobile device during the clinical mobility based assessment using the drift compensated velocity data.

Embodiments of the present technology include processing in real-time the locally logged inertial data of the user 110 to determine position and orientation of the mobile device 120 during the clinical mobility based assessment. In some embodiments the processing in real-time the locally logged inertial data of the user 110 to determine position and orientation of the mobile device during the clinical mobility based assessment comprises: segmenting and aligning the locally logged inertial data of the user 110 resulting in segmented and aligned inertial data of the user 110; integrating angular orientation of the segmented and aligned inertial data of the user 110 resulting in counterbalanced inertial data of the user 110; determining velocity of the mobile device during the clinical mobility based assessment using the counterbalanced inertial data of the user 110; drift compensating the velocity of the mobile device during the clinical mobility based assessment resulting in drift compensated velocity data; and determining the position and the orientation of the mobile device during the clinical mobility based assessment using the drift compensated velocity data.

Figure 3:
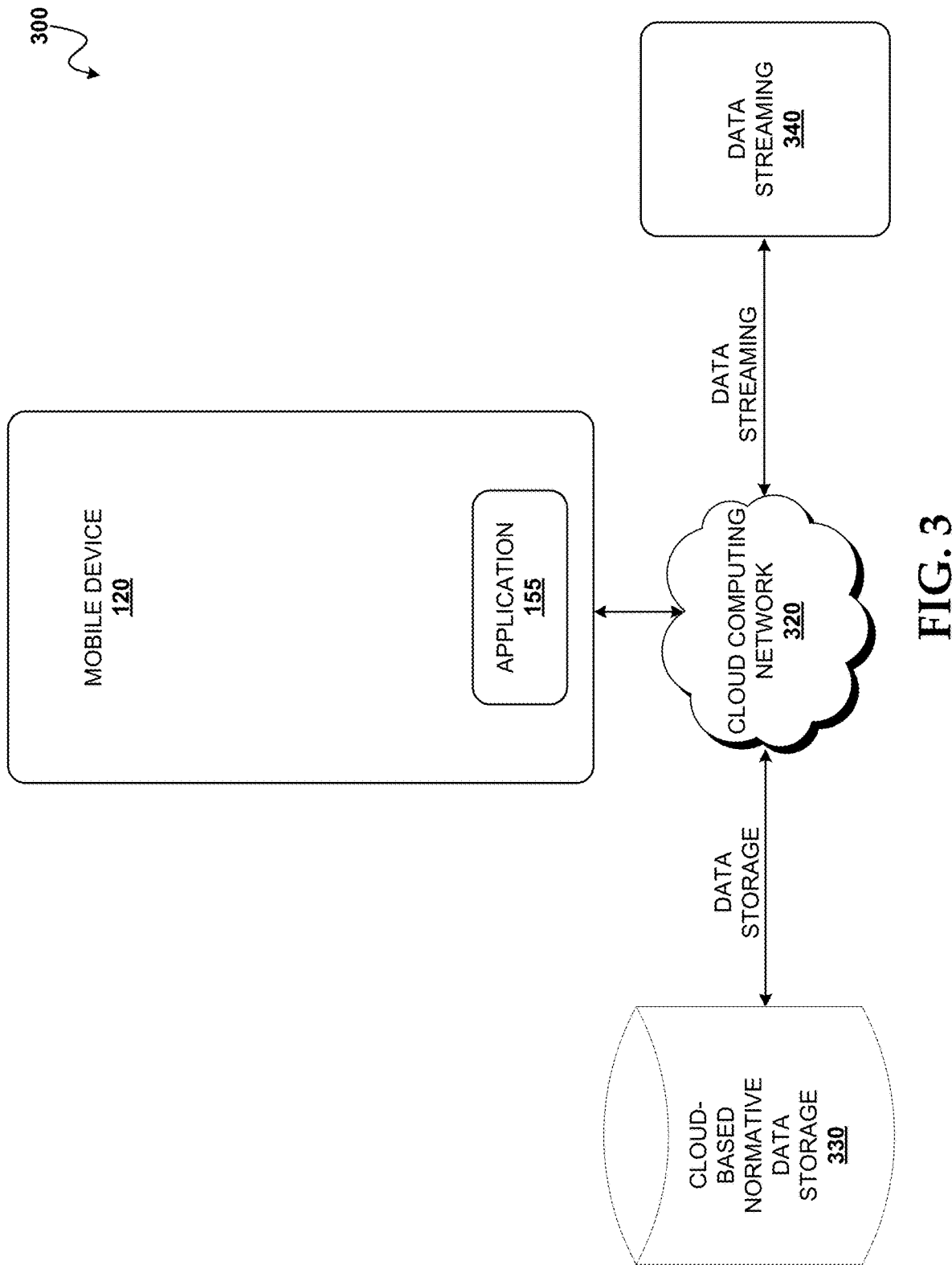
FIG. 3 shows a communication system between a system for monitoring movement capabilities of a user using clinical mobility based assessments and cloud-based platforms according to embodiments of the present technology.

FIG. 3 shows a communication system 300 between a system for monitoring movement capabilities of a user using clinical mobility based assessments and cloud-based platforms according to embodiments of the present technology. The communication system 300 comprises the mobile device 120 that comprises an application 155 (e.g., Electronic Caregiver application). The communication system 300 further comprises cloud computing network 320, cloud-based normative data storage 330, and data streaming 340. In various embodiments, application 155 communicates with the cloud computing network 320.

In general, the cloud computing network 320 is a cloud-based computing environment, which is a resource that typically combines the computational power of a large grouping of processors (such as within web servers) and/or that combines the storage capacity of a large grouping of computer memories or storage devices.

The cloud computing network 320 may be formed, for example, by a network of web servers that comprise a plurality of computing devices, such as the computer system 700, with each server (or at least a plurality thereof) providing processor and/or storage resources. These servers may manage workloads provided by multiple users (e.g., cloud resource customers or other users).

FIG. 4A shows results of an inertial data processing algorithm for analysis of a chair stand clinical mobility based assessment 400 according to embodiments of the present technology. For example, an inertial data processing algorithm used to process inertial data of the user that is indicative of movement capabilities of the user based on the clinical mobility based assessment may be the inertial data processing algorithm 200 shown in FIG. 2. In more detail, FIG. 4A shows segmenting and aligning the locally logged inertial data of the user 110 resulting in segmented and aligned inertial data of the user 110. For example, signal segmentation 405 of a plurality of signal segmentations is shown in FIG. 4A. More specifically, FIG. 4A shows analysis of a chair stand clinical mobility based assessment that is described in more detail in Example 1.

Figure 4B:
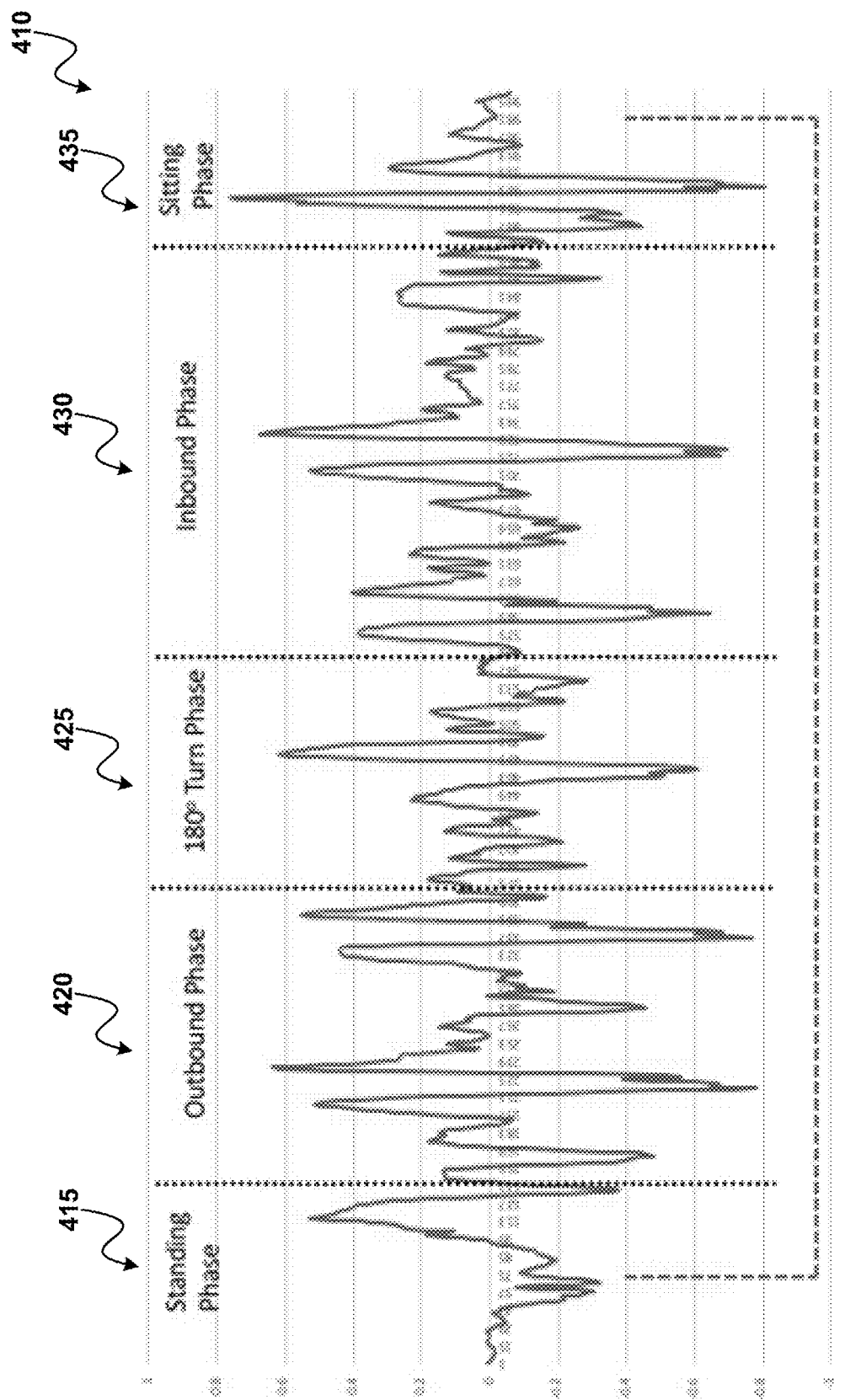
FIG. 4B depicts results of an inertial data processing algorithm for analysis of a timed up-and-go clinical mobility based assessment according to embodiments of the present technology.

FIG. 4B depicts results of the inertial data processing algorithm 200 for analysis of a timed up-and-go clinical mobility based assessment 410 according to embodiments of the present technology. In more detail, FIG. 4B shows analysis of a timed up-and-go clinical mobility based assessment 410 as described in more detail in Example 2.

FIG. 5A depicts a table 500 showing movement assessments for determination of functional movement capacity of the user 110 according to embodiments of the present technology. For example, a clinical mobility based assessment may be a motion task. In various embodiments a clinical mobility based assessment may be a test duration, a turning duration, a sit-to-stand duration, a stand-to-sit duration, a number of sit-to-stand repetitions completed within a predetermined period of time, and a number of stand-to-sit repetitions completed within a predetermined period of time. Exemplary clinical mobility based assessments (e.g., motion tasks) include timed up-and-go test, 30 second chair stand test, four stage balance test, gait analysis, functional reach test, sit and teach test, 5 chair stand test, 10 chair stand test, arm curl test, and postural stability. Table 500 further shows an area of assessment of the user 110 evaluated for each clinical mobility based assessment (e.g., motion task).

FIG. 5B depicts a table 510 showing features extracted from inertial data of the user 110 that describe functional movements following application analysis algorithms describing user functional movement capacity according to embodiments of the present technology. For example, determining features of functional movements of the user 110 based on the position and the orientation of the mobile device 120 during the clinical mobility based assessment, the features of functional movements including one or more of: time to completion of a task, rate to completion of a task, total repetitions of a task completed within a predetermined period of time, decay of repetitions of a task completed within a predetermined period of time, turn rate, anteroposterior sway, mediolateral sway, gait characteristics, total magnitude of displacement, vertical displacement, mediolateral displacement, and resultant displacement. Table 510 also shows features of the user 110 extracted for each clinical mobility based assessment (e.g., motion task).

Figure 6:
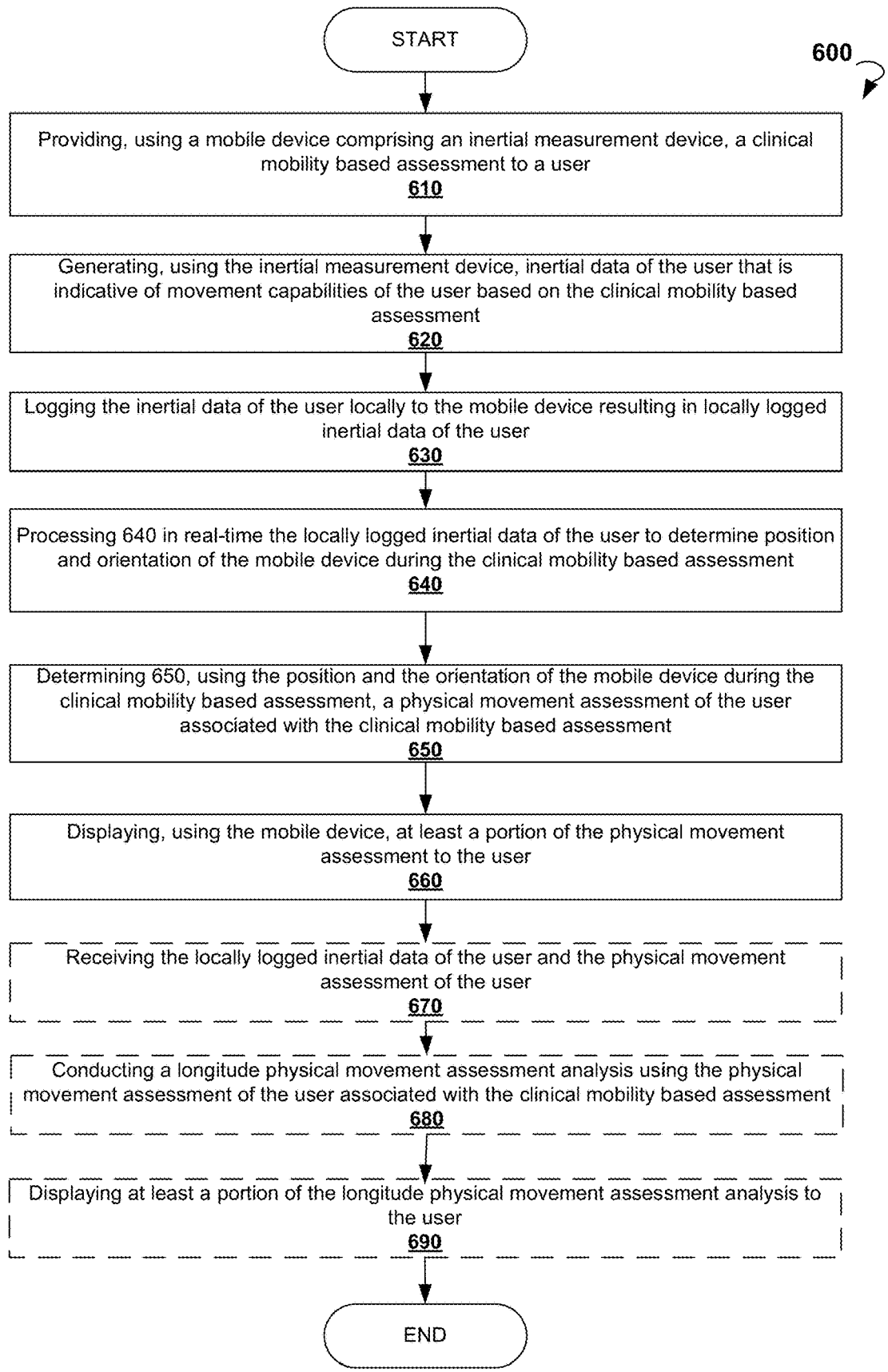
FIG. 6 shows depicts a process flow diagram showing a method for monitoring movement capabilities of a user using clinical mobility based assessments according to embodiments of the present technology.

FIG. 6 depicts a process flow diagram showing a method 600 for monitoring movement capabilities of a user using clinical mobility based assessments according to embodiments of the present technology. The method 600 may be performed by processing logic that may comprise hardware (e.g., dedicated logic, programmable logic, and microcode), software (such as software run on a general-purpose computer system or a dedicated machine), or a combination thereof. In one or more example embodiments, the processing logic resides at the mobile device 120, the inertial measurement device 130, the functional test system 170, the balance/stability system 180, and the gait analysis system 190, or the cloud-based normative data storage 330 or combinations thereof.

As shown in FIG. 6, the method 600 for monitoring movement capabilities of a user using clinical mobility based assessments comprises providing 610, using a mobile device comprising an inertial measurement device, a clinical mobility based assessment to a user. The method 600 may commence at generating 620, using the inertial measurement device, inertial data of the user that is indicative of movement capabilities of the user based on the clinical mobility based assessment. The method 600 may proceed with logging 630 the inertial data of the user locally to the mobile device resulting in locally logged inertial data of the user; and processing 640 in real-time the locally logged inertial data of the user to determine position and orientation of the mobile device during the clinical mobility based assessment. The method 600 may proceed with determining 650, using the position and the orientation of the mobile device during the clinical mobility based assessment, a physical movement assessment of the user associated with the clinical mobility based assessment; and displaying 660, using the mobile device, at least a portion of the physical movement assessment to the user.

In various embodiments, the method 600 optionally includes receiving 670 the locally logged inertial data of the user and the physical movement assessment of the user; conducting 680 a longitude physical movement assessment analysis using the physical movement assessment of the user associated with the clinical mobility based assessment; and displaying 690 at least a portion of the longitude physical movement assessment analysis to the user.

In various embodiments the conducting the longitude physical movement assessment analysis comprises: receiving a predetermined threshold of change in physical movement associated with a domain from a cloud-based normative data storage; comparing the physical movement assessment of the user with the predetermined threshold of change in physical movement; determining, based on the comparing, that the physical movement assessment exceeds the predetermined threshold of change in physical movement; and displaying, if the physical movement assessment exceeds the predetermined threshold of change in physical movement, a longitude mobility assessment to the user.

EXAMPLE 1

FIG. 4A shows results of the inertial data processing algorithm 200 for analysis of a chair stand clinical mobility based assessment 400 according to embodiments of the present technology. For example, a functional test may be an ability of the user 110 to complete chair stands. This particular area of testing provides valuable insight into lower extremity muscular strength of the user 110. One specific test, the 30-second chair stand, can be remotely assessed by the application 155. To achieve this, the user 110 assumes a seated position in a standard chair, opens the application 155 (e.g., Electronic Caregiver application) and selects the corresponding test (e.g., chair stand clinical mobility based assessment) from a drop down menu. Upon test selection, the inertial measurement device 130 of the mobile device 120 is activated and begins collecting inertial data of the user 110. After a 5 second countdown, the user 110 begins the chair stand test and completes as many sit-to-stand movements followed by stand-to-sit repetitions as possible in the allotted time. As depicted in FIG. 4A, the vertical acceleration signal can be utilized for assessing the number of repetitions completed during the test, which is the standard clinical variable assessed during the test. Assessing the number of repetitions completed is achieved through application of signal segmentation, which separates the signal into distinct segments based on a quantifiable spike in the magnitude of vertical acceleration and the application of a simple count function that determines the number of independent segments that were derived during processing. For example, the signal segmentation 405 of a plurality of signal segmentations is shown in FIG. 4A.

EXAMPLE 2

FIG. 4B depicts results of the inertial data processing algorithm 200 for analysis of a timed up-and-go clinical mobility based assessment 410 according to embodiments of the present technology. For example, a functional test utilized in a geriatric care provision setting is the timed up-and-go test. The timed up-and-go test requires the user 110 to start in a seated position in a standard chair, rise to a standing position, and walk a distance of 3 meters. At the 3 meter mark, the user 110 completes a 180° degree turn, walks back to the starting point, and then sits down in the chair they started in. As the timed up-and-go test is completed, a clinician typically records the time it takes the patient to complete the test.

In various embodiments, systems and methods of the present technology described herein are capable of performing the same assessment as a clinician on demand in various embodiments. As such, the user 110 assumes a seated position in a standard chair, opens the application 155 (e.g., Electronic Caregiver application), and selects a clinical mobility based assessment (i.e., the timed up-and-go clinical mobility based assessment) from the drop down menu on the mobile device 120. Upon test selection, the inertial measurement device 130 is activated and begins collecting inertial data of the user 110. After a 5 second countdown, the user 110 performs the timed up-and-go test from beginning to end. After returning to the seated position, the user selects the end test icon to terminate collection of inertial data. As the timed up-and-go test is completed, the signal segmentation algorithm segments the inertial data into a standing phase 415, an outbound phase 420 (i.e., outbound walking), a 180° turn phase 425 (i.e., turning), an inbound phase 430 (i.e., inbound walking), and a sitting phase 435. Following segmenting and aligning the locally logged inertial data of the user, a variety of features (e.g. time to test completion, magnitude of vertical acceleration during standing, and magnitude of vertical acceleration during sitting) are used to identify characteristics of functional decline of the user 110. For example, characteristics of functional decline may include an increase in the time to complete the timed up-and-go test, a decline in the peak and/or overall magnitude of vertical acceleration during the standing phase 415 or an increase in the peak and/or overall magnitude of vertical acceleration during the sitting phase 435.

EXAMPLE 3

Another common functional test utilized in a geriatric care provision setting is the postural stability test. The postural stability test requires the user 110 to maintain a static standing position for a period of time during which postural sway measurements are collected. As the postural stability test is completed, a clinician typically records the observed stability of the user 110 completing the postural stability test as well as the various magnitudes of acceleration that are indicative of postural sway. Again, systems and methods of the present technology including the application 155 (e.g., Electronic Caregiver application) are capable of performing the same assessment as the clinician on demand. As such, the user 110 assumes a standing position, opens the application 155 (e.g., Electronic Caregiver application) and selects the postural stability test from a drop down menu. Upon selection of the postural stability test, the inertial measurement device 130 in the mobile device 120 is activated and begins collecting inertial data of the user 110. After a 5 second countdown, the user 110 performs the postural stability test for a temporal period specified by the application 155. As the postural stability test is completed, the inertial data of the user 110 is processed and transposed into anteroposterior, mediolateral and resultant magnitudes (i.e., accelerometer data) and angular motion magnitudes about the anteroposterior, mediolateral and transverse axes (i.e., gyroscopic data). The accelerometer data and the gyroscopic data are analyzed to quantify the magnitude of sway along and about each bodily axis which can be used as an indicator of overall static stability and potential risk of falling of the user 110.

Figure 7:
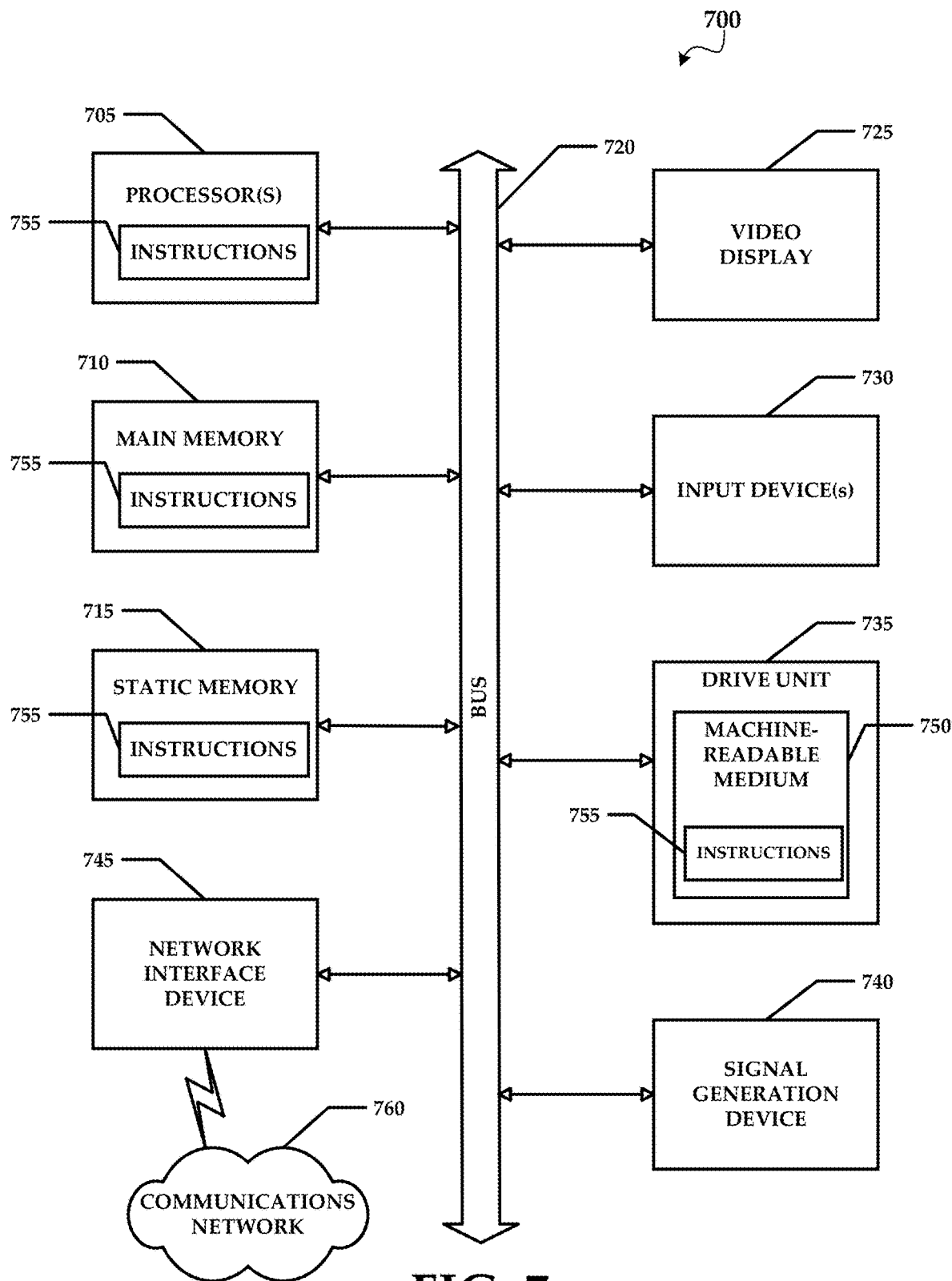
FIG. 7 illustrates an exemplary computer system that may be used to implement embodiments of the present technology.

FIG. 7 illustrates an exemplary computer system that may be used to implement embodiments of the present technology. FIG. 7 shows a diagrammatic representation of a computing device for a machine in the example electronic form of a computer system 700, within which a set of instructions for causing the machine to perform any one or more of the methodologies discussed herein can be executed. In example embodiments, the machine operates as a standalone device, or can be connected (e.g., networked) to other machines. In a networked deployment, the machine can operate in the capacity of a server, a client machine in a server-client network environment, or as a peer machine in a peer-to-peer (or distributed) network environment. The machine can be a personal computer (PC), tablet PC, game console, set-top box (STB), personal digital assistant (PDA), television device, cellular telephone, portable music player (e.g., a portable hard drive audio device), web appliance, or any machine capable of executing a set of instructions (sequential or otherwise) that specify actions to be taken by that machine. Further, while only a single machine is illustrated, the term "machine" shall also be taken to include any collection of machines that separately or jointly execute a set (or multiple sets) of instructions to perform any one or more of the methodologies discussed herein. Computer system 700 can be an instance of the mobile device 120, the inertial measurement device 130, the functional test system 170, the balance/stability system 180, and the gait analysis system 190, or the cloud-based normative data storage 330.

The example computer system 700 includes a processor or multiple processors 705 (e.g., a central processing unit (CPU), a graphics processing unit (GPU), or both), and a main memory 710 and a static memory 715, which communicate with each other via a bus 720. The computer system 700 can further include a video display unit 725 (e.g., a liquid-crystal display (LCD), organic light emitting diode (OLED) display, or a cathode ray tube (CRT)). The computer system 700 also includes at least one input device 730, such as an alphanumeric input device (e.g., a keyboard), a cursor control device (e.g., a mouse), a microphone, a digital camera, a video camera, and so forth. The computer system 700 also includes a disk drive unit 735, a signal generation device 740 (e.g., a speaker), and a network interface device 745.

The disk drive unit 735 (also referred to as the disk drive unit 735) includes a machine-readable medium 750 (also referred to as a computer-readable medium 750), which stores one or more sets of instructions and data structures (e.g., instructions 755) embodying or utilized by any one or more of the methodologies or functions described herein. The instructions 755 can also reside, completely or at least partially, within the main memory 710, static memory 715 and/or within the processor(s) 705 during execution thereof by the computer system 700. The main memory 710, static memory 715, and the processor(s) 705 also constitute machine-readable media.

The instructions 755 can further be transmitted or received over a communications network 760 via the network interface device 745 utilizing any one of a number of well-known transfer protocols (e.g., Hyper Text Transfer Protocol (HTTP), CAN, Serial, and Modbus). The communications network 760 includes the Internet, local intranet, Personal Area Network (PAN), Local Area Network (LAN), Wide Area Network (WAN), Metropolitan Area Network (MAN), virtual private network (VPN), storage area network (SAN), frame relay connection, Advanced Intelligent Network (AIN) connection, synchronous optical network (SONET) connection, digital T1, T3, E1 or E3 line, Digital Data Service (DDS) connection, Digital Subscriber Line (DSL) connection, Ethernet connection, Integrated Services Digital Network (ISDN) line, cable modem, Asynchronous Transfer Mode (ATM) connection, or an Fiber Distributed Data Interface (FDDI) or Copper Distributed Data Interface (CDDI) connection. Furthermore, communications network 760 can also include links to any of a variety of wireless networks including Wireless Application Protocol (WAP), General Packet Radio Service (GPRS), Global System for Mobile Communication (GSM), Code Division Multiple Access (CDMA) or Time Division Multiple Access (TDMA), cellular phone networks, Global Positioning System (GPS), cellular digital packet data (CDPD), Research in Motion, Limited (RIM) duplex paging network, Bluetooth radio, or an IEEE 802.11-based radio frequency network.

While the machine-readable medium 750 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media. Such media can also include, without limitation, hard disks, floppy disks, flash memory cards, digital video disks, random access memory (RAM), read only memory (ROM), and the like.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software programs for implementing the present method can be written in any number of suitable programming languages such as, for example, Hypertext Markup Language (HTML), Dynamic HTML, XML, Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, C #, .NET, Adobe Flash, Perl, UNIX Shell, Visual Basic or Visual Basic Script, Virtual Reality Markup Language (VRML), ColdFusion™ or other compilers, assemblers, interpreters, or other computer languages or platforms.

Thus, technology for monitoring movement capabilities of a user using clinical mobility based assessments is disclosed. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A system for monitoring movement capabilities of a user using clinical mobility-based assessments, the system comprising:
   a mobile device comprising an inertial measurement device, the inertial measurement device comprising:
      a gyroscope; and
      an accelerometer;
   at least one processor; and
   a memory storing processor-executable instructions, wherein the at least one processor is configured to implement the following operations upon executing the processor-executable instructions:
   providing a clinical mobility-based assessment to a user;
   generating, using the inertial measurement device, inertial data of the user that is indicative of movement capabilities of the user based on the clinical mobility-based assessment;
   logging the inertial data of the user locally to the mobile device resulting in locally logged inertial data of the user;
   processing in real-time the locally logged inertial data of the user to determine position and orientation of the mobile device during the clinical mobility-based assessment, wherein the processing in real-time of the locally logged inertial data of the user to determine position and orientation of the mobile device during the clinical mobility-based assessment comprises:
      segmenting and aligning the locally logged inertial data of the user resulting in segmented and aligned inertial data of the user;
      integrating angular orientation of the segmented and aligned inertial data of the user resulting in counterbalanced inertial data of the user;
      determining velocity of the mobile device during the clinical mobility-based assessment using the counterbalanced inertial data of the user;
      drift compensating the velocity of the mobile device during the clinical mobility-based assessment resulting in drift compensated velocity data; and
      determining the position and the orientation of the mobile device during the clinical mobility-based assessment using the drift compensated velocity data;
   wherein the at least one processor is further configured to implement the following operations upon executing the processor-executable instructions:
   determining, using the position and the orientation of the mobile device during the clinical mobility-based assessment, a physical movement assessment of the user associated with the clinical mobility-based assessment; and
   displaying at least a portion of the physical movement assessment to the user, wherein the displaying includes declines in the clinical mobility-based assessment.

2. The system as recited in claim 1, further comprising an interactive animated conversational graphical user interface displayed by the mobile device;
   wherein the at least one processor is further configured to implement an operation of displaying a representation of the clinical mobility based assessment via the interactive animated conversational graphical user interface.

3. The system as recited in claim 1, wherein the clinical mobility based assessment includes one or more of a test duration, a turning duration, a sit-to-stand duration, a stand-to-sit duration, a number of sit-to-stand repetitions completed within a predetermined period of time, and a number of stand-to-sit repetitions completed within a predetermined period of time.

4. The system as recited in claim 1, wherein the inertial data of the user that is indicative of movement capabilities of the user based on the clinical mobility-based assessment comprises gyroscope data generated using the gyroscope; and accelerometer data generated using the accelerometer.

5. The system as recited in claim 1, wherein the at least one processor is further configured to implement an operation of:
   determining features of functional movements of the user based on the position and the orientation of the mobile device during the clinical mobility-based assessment, the features of the functional movements including one or more of: time to completion of a task, rate to completion of a task, total repetitions of a task completed within a predetermined period of time, decay of repetitions of a task completed within a predetermined period of time, turn rate, anteroposterior sway, mediolateral sway, gait characteristics, total magnitude of displacement, vertical displacement, mediolateral displacement, and resultant displacement.

6. The system as recited in claim 1, wherein the physical movement assessment to the user includes one or more of a static stability of the user, dynamic stability of the user, postural stability of the user, balance of the user, mobility of the user, fall risk of the user, lower body muscular strength of the user, lower body muscular endurance of the user, lower body muscular flexibility of the user, upper body muscular strength of the user, and upper body muscular endurance of the user.

7. The system as recited in claim 1, wherein the at least one processor is further configured to implement operations of:
   receiving the locally logged inertial data of the user and the physical movement assessment of the user;
   conducting a longitude physical movement assessment analysis using the physical movement assessment of the user associated with the clinical mobility-based assessment; and
   displaying at least a portion of the longitude physical movement assessment analysis to the user.

8. The system as recited in claim 7, wherein the conducting the longitude physical movement assessment analysis comprises:
   receiving a predetermined threshold of change in physical movement associated with a domain from a cloud-based normative data storage;
   comparing the physical movement assessment of the user with the predetermined threshold of change in physical movement;
   determining, based on the comparing, that the physical movement assessment exceeds the predetermined threshold of change in physical movement; and
   displaying, when the physical movement assessment exceeds the predetermined threshold of change in physical movement, a longitude mobility assessment to the user.

9. A method for monitoring movement capabilities of a user using clinical mobility-based assessments, the method comprising:
   providing, using a mobile device comprising an inertial measurement device, a clinical mobility-based assessment to a user;
   generating, using the inertial measurement device, inertial data of the user that is indicative of movement capabilities of the user based on the clinical mobility-based assessment;
   logging the inertial data of the user locally to the mobile device resulting in locally logged inertial data of the user;
   processing in real-time the locally logged inertial data of the user to determine position and orientation of the mobile device during the clinical mobility-based assessment, wherein the processing in real-time the locally logged inertial data of the user to determine position and orientation of the mobile device during the clinical mobility based assessment comprises:
      segmenting and aligning the locally logged inertial data of the user resulting in segmented and aligned inertial data of the user;
      integrating angular orientation of the segmented and aligned inertial data of the user resulting in counterbalanced inertial data of the user;
      determining velocity of the mobile device during the clinical mobility-based assessment using the counterbalanced inertial data of the user;
      drift compensating the velocity of the mobile device during the clinical mobility-based assessment resulting in drift compensated velocity data; and
      determining the position and the orientation of the mobile device during the clinical mobility-based assessment using the drift compensated velocity data;
   the method further comprising:
   determining, using the position and the orientation of the mobile device during the clinical mobility-based assessment, a physical movement assessment of the user associated with the clinical mobility-based assessment; and
   displaying, using the mobile device, at least a portion of the physical movement assessment to the user, wherein the displaying includes declines in the clinical mobility-based assessment.

10. The method as recited in claim 9, further comprising:
   displaying a representation of the clinical mobility-based assessment via an interactive animated conversational graphical user interface displayed by the mobile device.

11. The method as recited in claim 9, wherein the clinical mobility-based assessment includes one or more of a test duration, a turning duration, a sit-to-stand duration, a stand-to-sit duration, a number of sit-to-stand repetitions completed within a predetermined period of time, and a number of stand-to-sit repetitions completed within a predetermined period of time.

12. The method as recited in claim 9, wherein the inertial data of the user that is indicative of the movement capabilities of the user based on the clinical mobility-based assessment comprises gyroscope data generated using a gyroscope; and accelerometer data generated using an accelerometer.

13. The method as recited in claim 9, further comprising:
   determining features of functional movements of the user based on the position and the orientation of the mobile device during the clinical mobility-based assessment, the features of functional movements including one or more of: time to completion of a task, rate to completion of a task, total repetitions of a task completed within a predetermined period of time, decay of repetitions of a task completed within a predetermined period of time, turn rate, anteroposterior sway, mediolateral sway, gait characteristics, total magnitude of displacement, vertical displacement, mediolateral displacement, and resultant displacement.

14. The method as recited in claim 9, wherein the physical movement assessment to the user includes one or more of a static stability of the user, dynamic stability of the user, postural stability of the user, balance of the user, mobility of the user, fall risk of the user, lower body muscular strength of the user, lower body muscular endurance of the user, lower body muscular flexibility of the user, upper body muscular strength of the user, and upper body muscular endurance of the user.

15. The method as recited in claim 9, further comprising:
   receiving the locally logged inertial data of the user and the physical movement assessment of the user;
   conducting a longitude physical movement assessment analysis using the physical movement assessment of the user associated with the clinical mobility-based assessment; and
   displaying at least a portion of the longitude physical movement assessment analysis to the user.

16. A non-transitory computer readable medium having embodied thereon instructions being executable by at least one processor to perform a method for monitoring movement capabilities of a user using clinical mobility-based assessments, the method comprising:
   providing, using a mobile device comprising an inertial measurement device, a clinical mobility-based assessment to a user;
   generating, using the inertial measurement device, inertial data of the user that is indicative of movement capabilities of the user based on the clinical mobility-based assessment;
   logging the inertial data of the user locally to the mobile device resulting in locally logged inertial data of the user;
   processing in real-time the locally logged inertial data of the user to determine position and orientation of the mobile device during the clinical mobility-based assessment, wherein the processing in real-time the locally logged inertial data of the user to determine position and orientation of the mobile device during the clinical mobility-based assessment comprises:
      segmenting and aligning the locally logged inertial data of the user resulting in segmented and aligned inertial data of the user;
      integrating angular orientation of the segmented and aligned inertial data of the user resulting in counterbalanced inertial data of the user;
      determining velocity of the mobile device during the clinical mobility based assessment using the counterbalanced inertial data of the user;
      drift compensating the velocity of the mobile device during the clinical mobility-based assessment resulting in drift compensated velocity data; and
      determining the position and the orientation of the mobile device during the clinical mobility-based assessment using the drift compensated velocity data;
   the method further comprising:
   determining, using the position and the orientation of the mobile device during the clinical mobility-based assessment, a physical movement assessment of the user associated with the clinical mobility-based assessment; and
   displaying, using the mobile device, at least a portion of the physical movement assessment to the user, wherein the displaying includes declines in the physical movement assessment.

* * * * *